(12) United States Patent
Wilson et al.

(10) Patent No.: US 8,477,003 B2
(45) Date of Patent: Jul. 2, 2013

(54) APPARATUS FOR GENERATING A MULTI-VIBRATIONAL FIELD

(76) Inventors: Gary Dean Wilson, Dolan Springs, AZ (US); Michael Dean Brown, White Hills, AZ (US)

(*) Notice: Subject to any disclaimer, the term of this patent is extended or adjusted under 35 U.S.C. 154(b) by 0 days.

(21) Appl. No.: 13/262,227

(22) PCT Filed: Mar. 29, 2010

(86) PCT No.: PCT/US2010/029017
§ 371 (c)(1),
(2), (4) Date: Sep. 29, 2011

(87) PCT Pub. No.: WO2010/114788
PCT Pub. Date: Oct. 7, 2010

(65) Prior Publication Data
US 2012/0038441 A1    Feb. 16, 2012

Related U.S. Application Data

(60) Provisional application No. 61/164,549, filed on Mar. 30, 2009.

(51) Int. Cl.
*H01F 1/00* (2006.01)
(52) U.S. Cl.
USPC .......................................... 335/296; 335/209

(58) Field of Classification Search
USPC .......................................... 335/209, 296–298
See application file for complete search history.

(56) References Cited

U.S. PATENT DOCUMENTS

| | | | | |
|---|---|---|---|---|
| 2,723,323 | A * | 11/1955 | Niemi | 335/88 |
| 3,698,661 | A * | 10/1972 | Wyatt | 244/166 |
| 2005/0206485 | A1* | 9/2005 | Godoy | 335/132 |
| 2010/0001204 | A1* | 1/2010 | White | 250/398 |

* cited by examiner

*Primary Examiner* — Bernard Rojas
(74) *Attorney, Agent, or Firm* — Schmeiser, Olsen & Watts LLP; Jordan M. Meschkow; Brandt D. Madsen

(57) ABSTRACT

An apparatus may deliver multi-vibrational electromagnetic (MVEM) fields which are independent but may work simultaneously. The MVEM fields may be used in many applications, including eliminating calcium build-up in pipes, reducing soap usage in laundry, reducing salt usage in water softeners, reducing chlorine use in pools, inhibiting algae growth, increasing water clarity, restructuring or inhibiting nitrates, restructuring or inhibiting tannins, restructuring or inhibiting calcium salts and other minerals, treating pain, treating inflammation, enhancing after-surgery healing, and improving circulation in treated areas of animals and humans. The apparatus may be formed from a plurality of wire-wrapped rods connected to a power supply. The plurality of rods may be incased in flexible foam and wrapped in a fabric outer covering.

17 Claims, 8 Drawing Sheets

APPARATUS FOR GENERATING A MULTI-VIBRATIONAL FIELD

CROSS-REFERENCE TO RELATED APPLICATIONS

This application claims the benefit of U.S. Provisional patent application No. 61/164,549 filed Mar. 30, 2009.

BACKGROUND OF THE INVENTION

The present invention generally relates to electromagnetism and, more particularly, to an apparatus that may deliver electromagnetic multi-vibrations fields that are independent but work simultaneously.

Magnetic fields have been used in various applications, such as therapeutic applications for treating the human body and water cleaning applications. A conventional electromagnetic water treatment apparatus may include an electric field and a magnetic field to prevent the occurrence and attachment of scale and rust along a channel used for the circulation of water. The presently available electromagnetic water treatment apparatus is so designed that a pair of permanent magnets and a pair of electrodes, composed of different metals, are attached to a casing, and along with the casing, collectively define a water passage.

According to the principle incorporated into this conventional apparatus, a magnetic field, which is generated by the permanent magnets, and an electric field, which is generated by a weak current that is fed to the electrodes, are applied to water flowing through the water passage, which is defined by the casing and the permanent magnets. The fields generated by conventional water treatment apparatus may hold metal shavings due to the magnetic field generated. Such an electromagnetic field may not be suitable for use in other applications, such as human therapeutic applications.

As can be seen, there is a need for an apparatus to generate an electromagnetic field that may be used in various applications, such as therapeutic applications for humans, water treatment and purification and the like.

SUMMARY OF THE INVENTION

In one aspect of the present invention, an apparatus comprises a plurality of rods; a non-conductive coating on at least a portion of each of the rods; a wire wrapped around the non-conductive coating of each of the rods; one end of the wire of a first rod connected to a first line of a DC power supply; a second end of the wire of a first rod connected to a wire end of an adjacent rod; one end of the wire of the last rod connected to a second line of the DC power supply; a second end of the wire of the last rod connected to a wire end of an adjacent rod; and each of the plurality of rods between the first rod and the last rod having first and second ends of wire connected to wire ends of each adjacent rod.

In another aspect of the present invention, a method for generating a multi-vibrational electromagnetic field comprises moving current through a plurality of copper wire coils, each of the copper wire coils wrapped around a rod, each of the rods disposed substantially parallel to each other.

In a further aspect of the present invention, an electromagnetic apparatus for delivering multi-vibrational fields comprises a plurality of spaced apart elongated rods with opposing ends, the rods partially covered with a non-conductive coating leaving the opposing ends of the rods uncovered; copper wire wrapped around each of the plurality of elongated rods, over the non-conductive coating, forming a plurality of copper coils connected in sequence to a power supply; a spacer strip attached to each end of the elongated rods; and a flexible housing for containing the plurality of copper coils.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, an embodiment of the present invention provides a soft wave apparatus that may deliver multi-vibrational electromagnetic (MVEM) fields which are independent but may work simultaneously. The MVEM fields may be used in many applications, including eliminating calcium build-up in pipes, reducing soap usage in laundry, reducing salt usage in water softeners, reducing chlorine use in pools, inhibiting algae growth, increasing water clarity, restructuring or inhibiting nitrates, restructuring or inhibiting tannins, restructuring or inhibiting calcium salts and other minerals, treating pain, treating inflammation, enhancing after-surgery healing, and improving circulation in treated areas of animals and humans.

In an exemplary embodiment, the soft wave apparatus may be formed from a plurality of wire-wrapped rods connected to a power supply. The plurality of rods may be incased in flexible foam and wrapped in a fabric outer covering.

Figure 1:
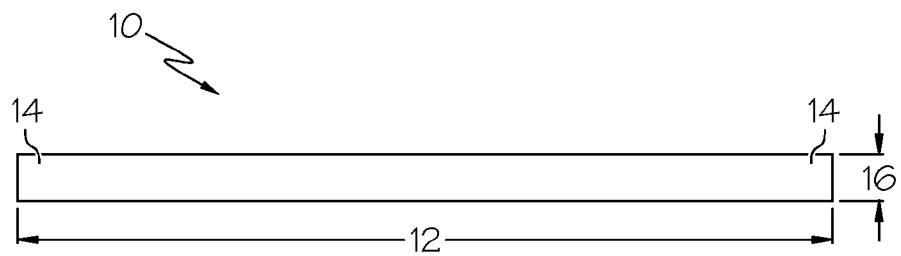
FIG. 1 is a side view of a rod used in an embodiment of the present invention.

Referring to FIG. 1, a rod 10 may be formed by cutting the rod 10 to the appropriate length 12. The ends 14 of the rods may be ground to avoid sharp edges. The length 12 of the rod 10 may vary with its intended application and may be from about 3 inches to about 12 inches, typically from about 4 inches to about 10 inches. The rod 10 may have a diameter 16 that may vary with its intended application and may be from about 1/16 inch to about 1/2 inch, typically about 1/8 inch to about 1/4 inch. The rod 10 may be made from a metal, typically a conductive metal, such as cold rolled steel.

Figure 2:
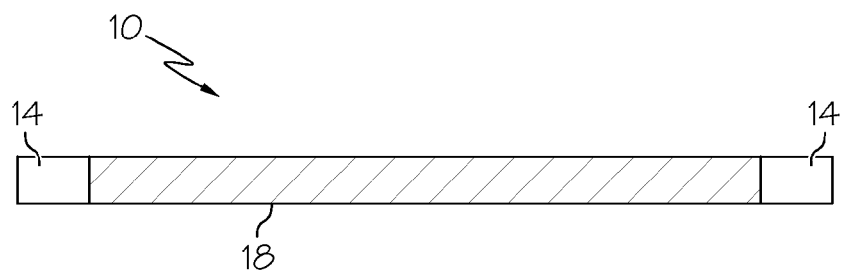
FIG. 2 is a side view of the rod of FIG. 1 wrapped in a non-conductive coating, according to an embodiment of the present invention.
Figure 3:
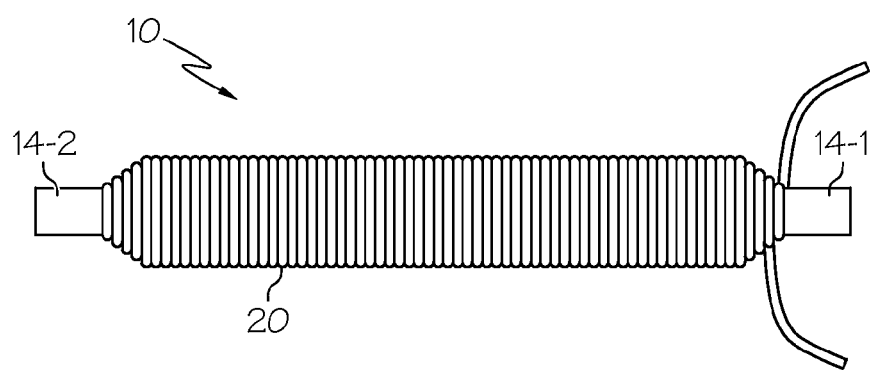
FIG. 3 is a side view of the coated rod of FIG. 2 wrapped with copper wire, according to an embodiment of the present invention.

Referring to FIGS. 2 and 3, the rod 10 may be wrapped with a non-conducting coating 18, with about 1/2 inch bare at each of the ends 14. The rod 10 may be wrapped with a conducting wire 20, such as a copper wire. The wire 20 may wrap from one end 14-1 of the rod 10 to the other end 14-2 of the rod 10. The wire 20 may be wrapped upon itself so that the wire begins and ends at the same end 14-1 of the rod 10. For example, four layers of wire 20 (from end 14-1 to end 14-2, from end 14-2 to end 14-1, from end 14-1 to end 14-2, and from end 14-2 to end 14-1) may be wrapped around the rod 10. The wire 20 may be a copper wire between about 36 gauge to about 10 gauge, typically from about 28 gauge to about 18 gauge.

Figure 4:
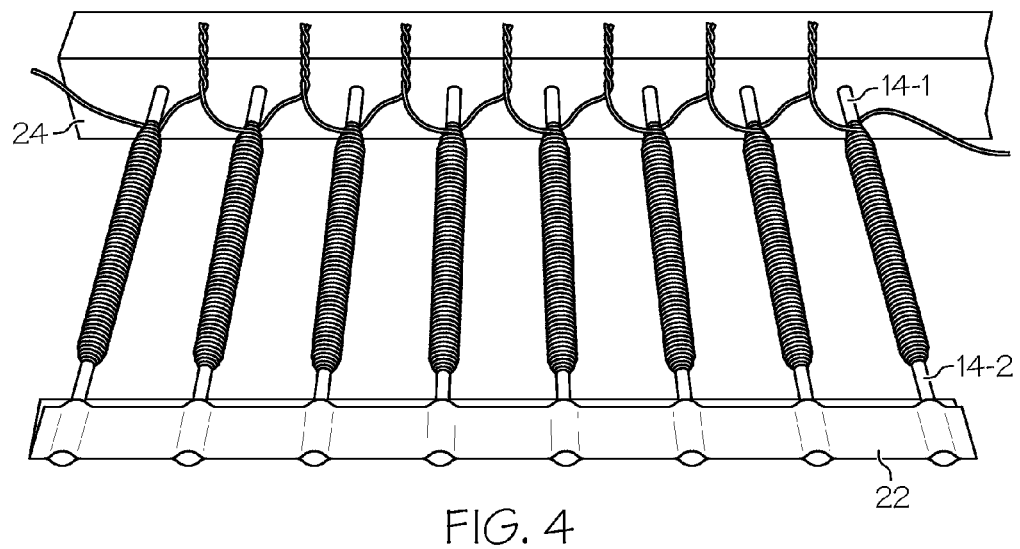
FIG. 4 is a perspective view of a plurality of the wire-wrapped rods of FIG. 3, connected in parallel, according to an embodiment of the present invention.

Referring now to FIG. 4, a plurality of rods 10 may be wrapped with wire 20, as described above. The rods 10 may be laid out substantially parallel to each other. One end 14-2 of the rods 10 may be connected with a separation strip 22. The other end 14-1 of the rods 10 may be temporarily inserted into a spacer jig 24. Typically, between 3 and 30 rods 10 may be used, often between 5 and 20 rods are used. The spacing between the rods 10 may be between 1/2 inch and about 2 inches. The number of rods, the number of windings on the rods, and the spacing between the rods may be a function of the intended use of the soft wave apparatus. For example, for calcium control, salt reduction and therapeutic applications, the spacing between rods 10 may be about 1.375 inches.

Figure 5:
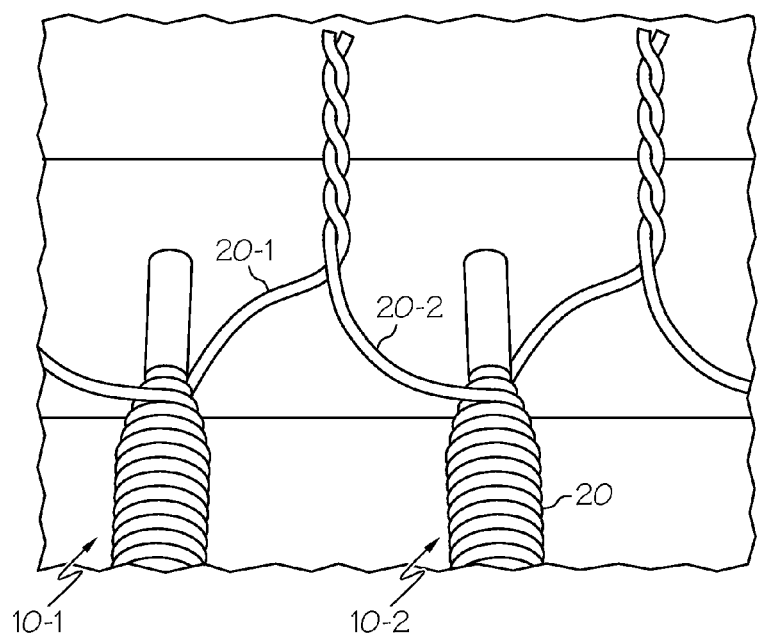
FIG. 5 is a close-up view of the connection between adjacent coils, according to an embodiment of the present invention.
Figure 6:
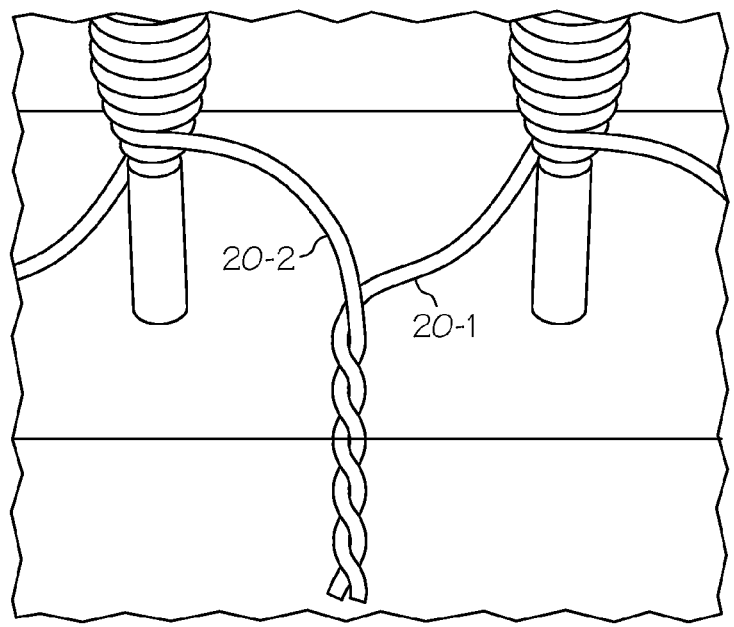
FIG. 6 is a close-up view of the connection of FIG. 5.

Referring to FIGS. 5 and 6, an inner wire end 20-1 of the wire 20 of one rod 10-1 may be electrically connected to an outer wire end 20-2 of the wire 20 of an adjacent rod 10-2. This inner/outer electrical connection sequence may be repeated for each of the rods 10 in the plurality of rods. The wires ends 20-1, 20-2 may be trimmed and soldered together as shown in FIG. 6.

Figure 7:
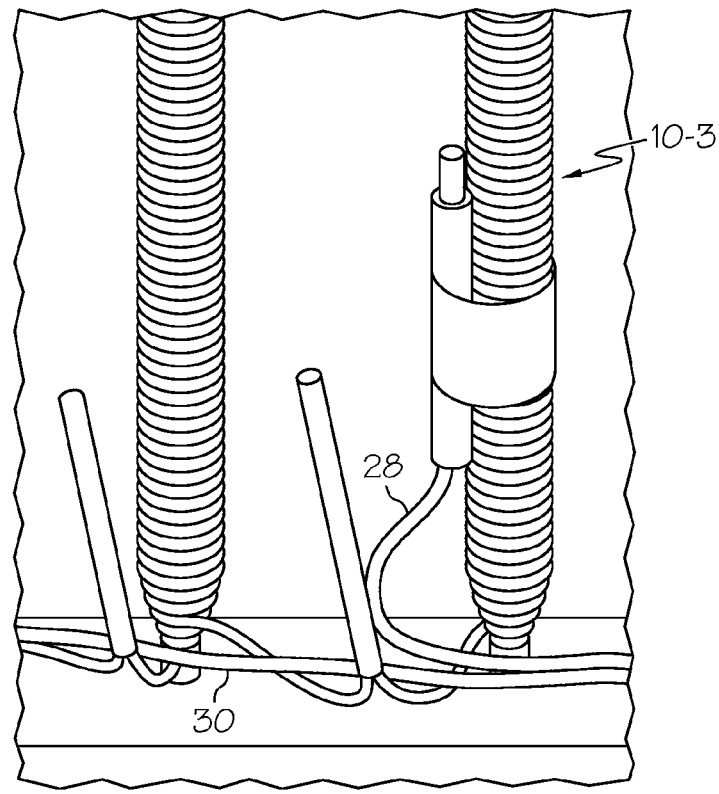
FIG. 7 is a close-up view of the connection of FIG. 5 shrink-wrapped according to an embodiment of the present invention.
Figure 8:
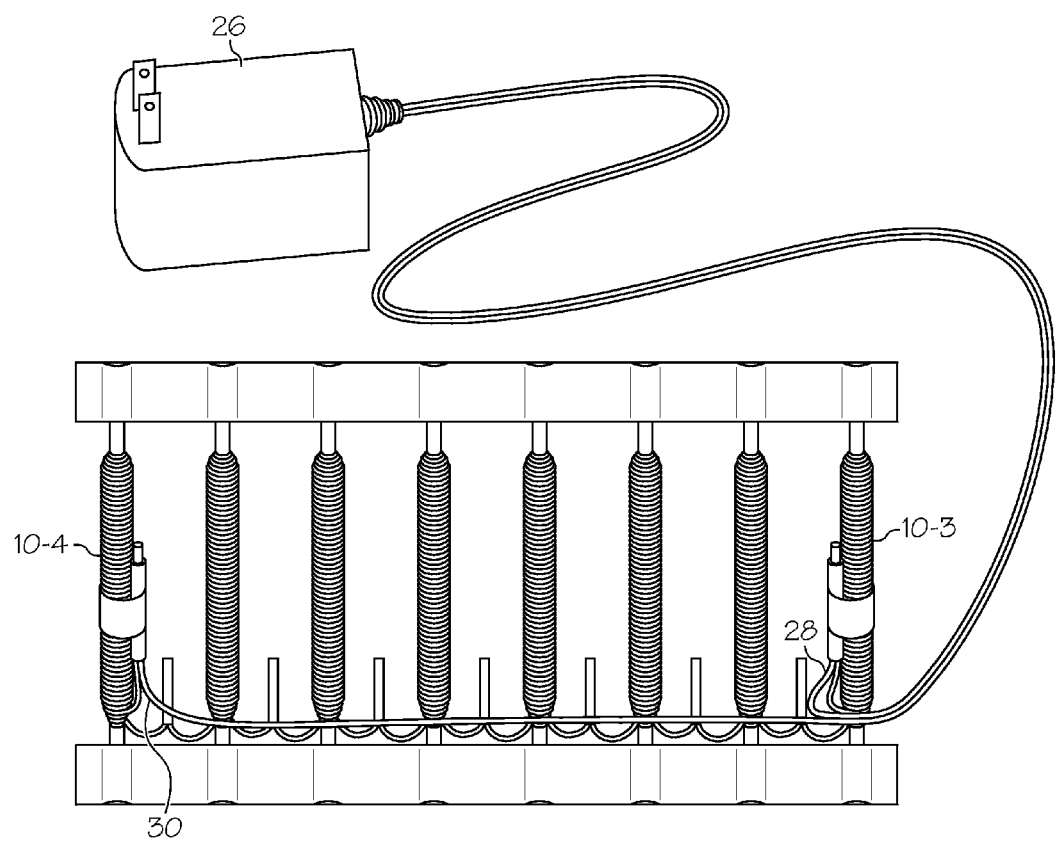
FIG. 8 is a perspective view of a plurality of wire-wrapped rods of FIG. 3, connected in parallel prior to testing a Gauss field, according to an embodiment of the present invention.
Figure 9:
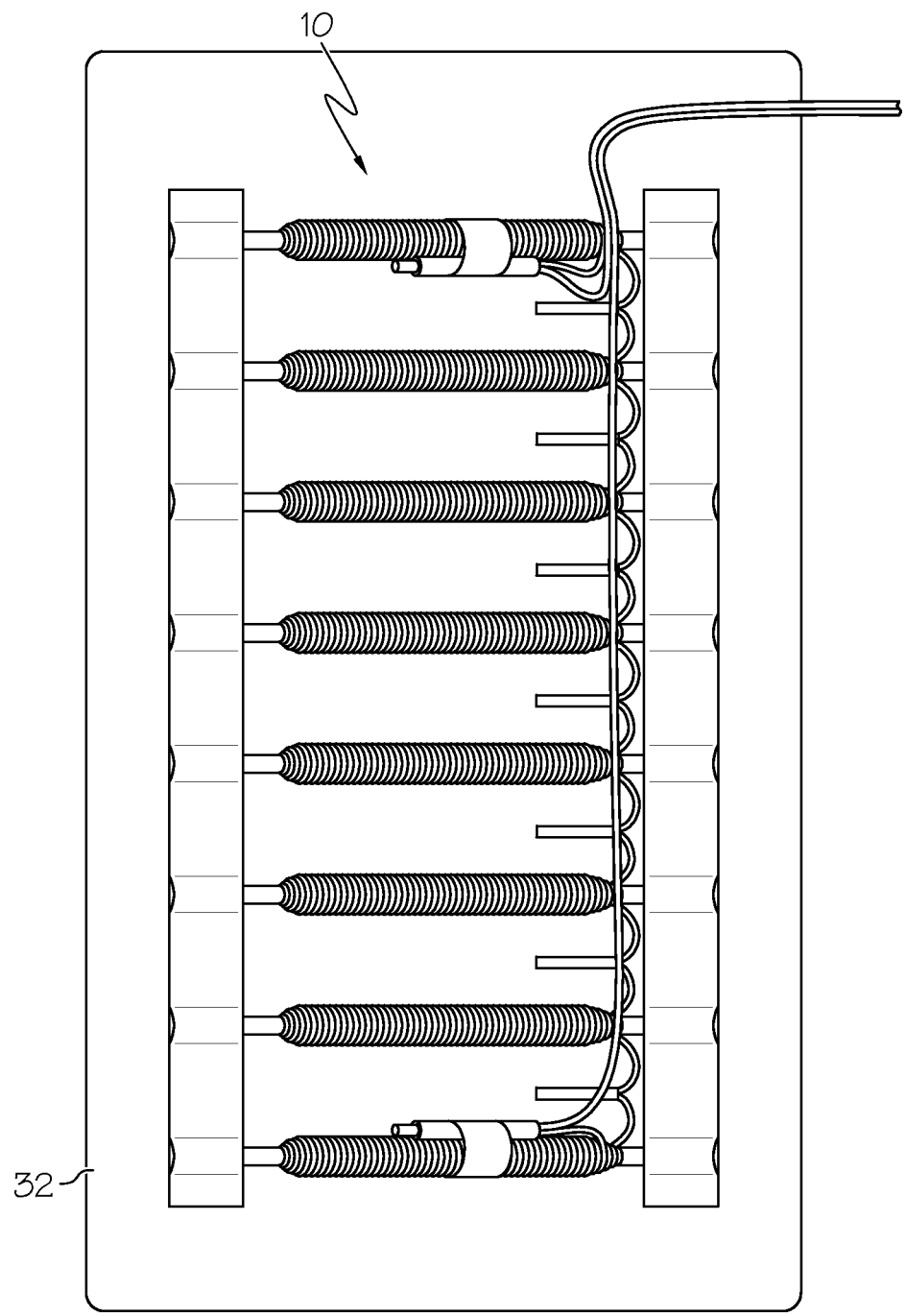
FIG. 9 is a perspective view of the plurality of wire-wrapped rods of FIG. 8, installed into a foam pad, according to an embodiment of the present invention.
Figure 10:
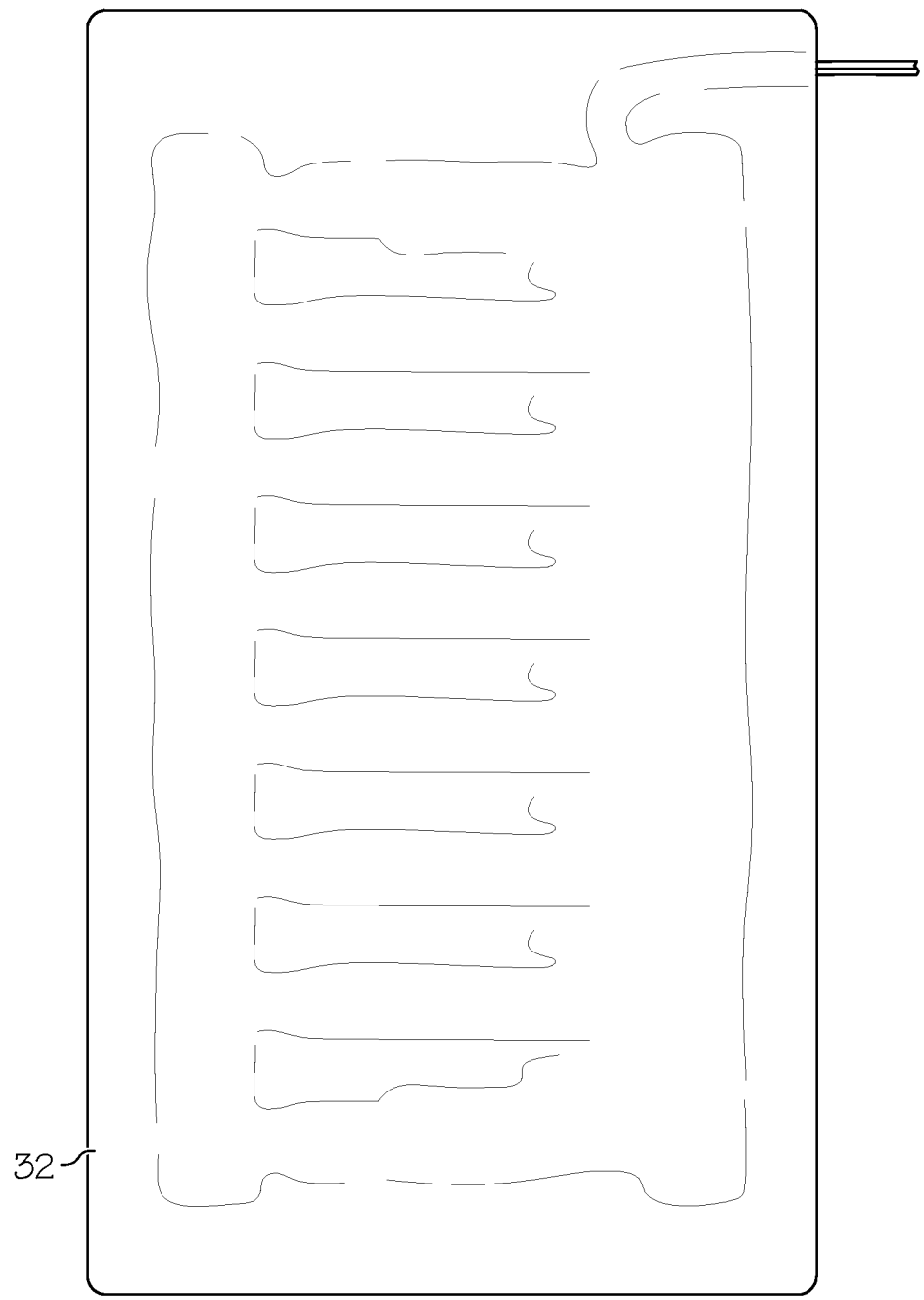
FIG. 10 is a perspective view of the installed rods of FIG. 9, fully encased in a foam pad, according to an embodiment of the present invention.

Referring to FIGS. 7 and 8, an alternating current (AC) to direct current (DC) transformer 26 may be connected to the rods 10. A positive DC lead 28 may connect to a first one of the rods 10-3 and a negative DC lead 30 may connect to a last one of the rods 10-4. The polarity of the above described connections may be reversed. The soldered wire ends 20-1, 20-2 may be shrink-wrapped with conventional shrink wrap tape. A spacer strip 32 may replace the spacer jig 24. The spacer strip 32 and the separation strip 22 may be formed of the same or different materials. The strips 32, 22 may be flexible, yet retain the spacing between adjacent rods 10. The transformer 26 may be connected to a power source, such as typical 60 Hertz (Hz) 105-120 volts (V) AC and the Gauss field may be tested with a conventional Gauss field meter, for example.

The transformer 26 may deliver DC voltage and current that may vary with the intended use of the soft wave apparatus. For example, the transformer 26 may deliver from about 3 V to about 30 V DC, typically from about 5 V to about 24 V DC. The transformer 26 may deliver from about 0.3 to about 5 amps (A), typically from about 1 to about 3 Å.

Figure 11:
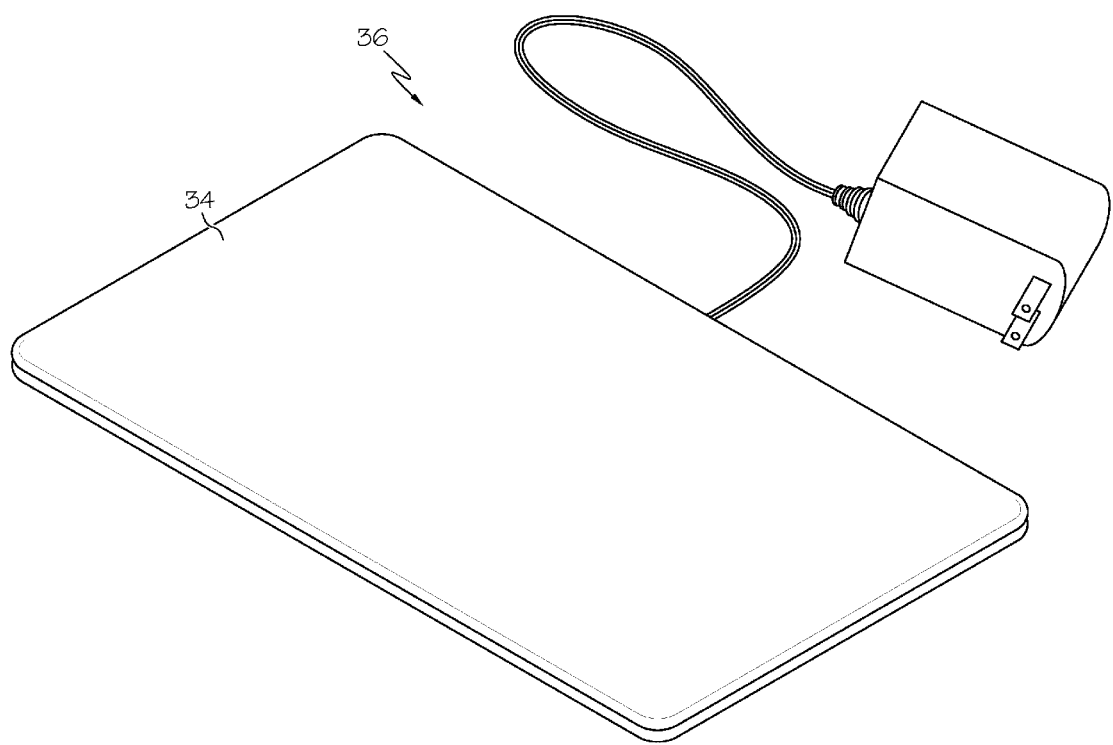
FIG. 11 is a perspective view of a soft wave apparatus, according to an embodiment of the present invention.
Figure 12:
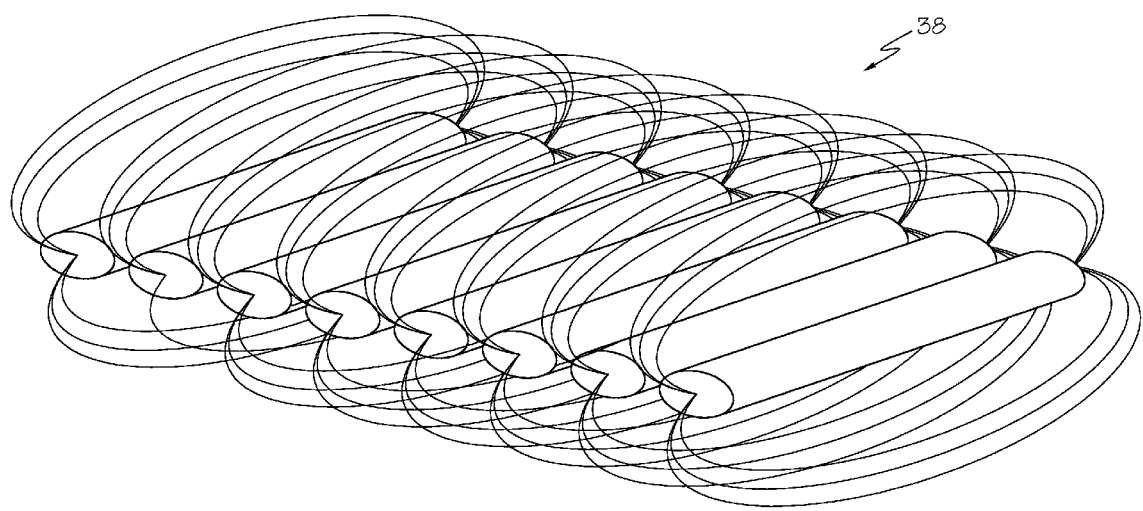
FIG. 12 is a perspective view of the electromagnetic Gauss field generated by the soft wave apparatus of FIG. 11.

Referring to FIGS. 9 through 12, the electrically connected rods 10 may be sealed in a foam pad 32. The foam pad 32 may be trimmed, if necessary, and the finished product may optionally be wrapped in an outer covering 34, as shown in FIG. 11. The resulting soft wave apparatus 36 may create an electromagnetic Gauss field 38, as shown in FIG. 12. The soft wave apparatus 36 may be used in various applications as described below.

Salt reduction in a water softener may be achieved by wrapping the soft wave apparatus 36 around a water pipe before it enters the softener. The salt settings may then be reduced by about 50% or more. Salt usage field testing has shown a 70% reduction in salt usage while maintaining 0 to 4 grains of water hardness.

Calcium control may be achieved by wrapping the soft wave apparatus 36 around a main water line. For even better results, the soft wave apparatus 36 may be wrapped around the main water line and the hot side of a water heater. Such a system may reduce or prevent calcium buildup in all water uses. This system may also reduce the amount of soap for laundry from about 1 cup to about 1/8 cup.

By wrapping the soft wave apparatus 36 around a circulation line of a swimming pool, chlorine usage was reduced by 66% while still maintaining the required residual chlorine levels. New calcium scale build-up was prevented, water clarity was improved and algae growth was inhibited.

For human and pet use, the soft wave apparatus 36 may be placed over a sore, inflamed, or injured area. The soft wave apparatus 36 may, for example, help relieve back and joint pain without the use of drugs.

The soft wave apparatus 36 of the present invention may also be used in order to improve fuel economy in cars by wrapping the apparatus 36 around the fuel line. Along these same lines, the soft wave apparatus 26 may also be used to improve the efficiency of butane and propane systems.

The soft wave apparatus 36 may be used to control calcium buildup in boilers, chillers, plumbing fixtures and equipment without chemical use.

While not relying on any single mode of operation of the present invention, the soft wave apparatus 36 may use electromagnetic impulses to restructure minerals and water molecules. The flux field of the soft wave apparatus 36 may travel with the flow of the water for a better, longer and stronger treatment, delivering optimum results. As water flows through a magnetic field, the molecules align. The soft wave apparatus 36 may use a pulsing electromagnetic field (PEMF) to align the molecules in a uniform directional field. Water may regain its solvency and may not allow minerals to form hard crystals of scale. The electromagnetic field generated by the soft wave apparatus 36 may move with the flow of the water, aligning the molecules and separating out the calcium. By treating the water instead of the calcium, the water may not bond with the calcium. The calcium may crystallize starving bacteria and not allow the calcium to bond in pipes, on fixtures in water heaters, or on glass or tile.

EXAMPLES

Example 1

Reduction of Nitrates/Nitrites

A manufacturer of health foods in Central Texas has a water softener and a reverse osmosis installed in their plant to remove hardness and nitrate/nitrites in the water. Nitrates/nitrites tested 1.0 ppm. A soft wave apparatus, according to an embodiment of the present invention, was installed to reduce salt usage and improve the efficiency of the reverse osmosis. The nitrate/nitrite levels tested zero after the installation of the soft wave apparatus.

Example 2

Water Discoloration from Vegetation

Last summer on Father's Day weekend, a pool that had been opened for 6-7 weeks had cloudy water that the pool service company could not clear up. The pool company had closed/covered the pool (for winterizing) with a large amount of leaves at the bottom. A soft wave apparatus, according to an embodiment of the present invention, was installed on the pool. The installation was as described above and the cloudy water cleared up by the very next day. It was also noticed that the usual negative effects (dry skin and hair, burning eyes and chlorine order) of the chlorine were not present. Days later, the pool clarity kept increasing. The pool was about 35,000 gallons and included sand filtration and a gas heater. The pool water temperature is normally kept around 85 degrees.

Example 3

Tannins Removed from Water

A home with a Culligan softener and a pool, all on well water, had a complaint of yellow water (lab analysis showed presence of tannins). Three soft wave apparatus, according to an embodiment of the present invention, were installed one on the well, one on the pool and one inline before the softener. Lab tested 0 tannins and TDS (Total Dissolved Solids) dropped 300 ppm from 1000 pmm. Home owner took pictures of their crystal blue pool (first time clear in 8 yrs).

Example 4

Water Softener Salt Reduction 5 Month Ongoing Test

Two hotels next to each other had the same water source. Both had Culligan® water softeners and both were monitored weekly by Culligan. The water at both facilities was tested and monitored daily by the hotel's Director of Engineering. Softeners with a soft wave apparatus, according to an embodiment of the present invention, consistently tested 0 to 4 grains hard (depending on the time of the last regeneration).

Cold side water, by-passed by the water softener, tested 16 grains hard. The use of the water softeners without the soft wave apparatus tested 7 to 10 grains hard on the hot side.

The Head of House Keeping (unaware of the ongoing tests) was asked by Engineering to test the water at both hotels. At one hotel (with the installed soft wave apparatus), towels and linens were softer and whiter and it was reported that the water tasted better.

Four months into the test, Engineering had House Keeping eliminate soap in the laundry and use only the bluing and bleach products. The hotel with the soft wave apparatus still had the whiter and softer linens.

Example 5

Hotel Swimming Pool

Chemicals used in the swimming pool were monitored and dispensed electronically. Chlorine usage was 15 gallons per day prior to the installation of the soft wave apparatus, according to an embodiment of the present invention.

One week after installation of the soft wave apparatus, chlorine usage was 5 gallons per day while still maintaining the required 4.0 PPM to 5.0 PPM chlorine. Two weeks after install, the calcium ring on the pool tile removed easily with a non-scratch sponge.

Example 6

Water Softener Salt Reduction

A water softener (Kenmore, 1 cube) was installed on a home in Fort Mojave in May 2009. At the same time a new water heater and a soft wave apparatus, according to an embodiment of the present invention, was installed. Initially, water was 75 grains hard. There were 8 family members. The water softener's salt setting was set for 30 grains hard (57% usage reduction). In February, the water was tested for hardness. Raw water tested at 73 grains hard. Treated water was tested at 4 grains hard. At time of test, water softener had not regenerated for 1½ days.

The water heater was drained for the first time since installation (10 months) and the water was flushing clean with no residue.

Example 7

Water Softener Salt Reduction

Hardness was set at 50 grains hard. The home still had problems with calcium build up. The settings were changed to 10 grains hard, and the soft wave apparatus, according to an embodiment of the present invention, was installed. No more calcium buildup was observed and the existing calcium dissolved naturally.

It should be understood, of course, that the foregoing relates to exemplary embodiments of the invention and that modifications may be made without departing from the spirit and scope of the invention as set forth in the following claims.

We claim:

1. An apparatus comprising:
   a plurality of rods;
   a non-conductive coating on at least a portion of each of the rods;
   a wire wrapped around the non-conductive coating of each of the rods;
   one end of the wire of a first rod connected to a first line of a DC power supply;
   a second end of the wire of a first rod connected to a wire end of an adjacent rod;
   one end of the wire of the last rod connected to a second line of the DC power supply;
   a second end of the wire of the last rod connected to a wire end of an adjacent rod;
   each of the plurality of rods between the first rod and the last rod having first and second ends of wire connected to wire ends of each adjacent rod; and
   a felxible spacer strip connecting ends of each of the plurality of rods.

2. The apparatus of claim 1, wherein the rods are from about 4 to about 10 inches long and have a diameter from about ⅛ to about ¼ inch.

3. The apparatus of claim 1, wherein the non-conductive coating covers each of the rods except for about ½ inch at each end of each rod.

4. The apparatus of claim 1, wherein the wire is a copper wire.

5. The apparatus of claim 1, wherein the wire is wrapped at least once from one end of the non-conductive coating to the other end of the non-conductive coating and back to the original end.

6. The apparatus of claim 5, wherein an inner wire end of one rod attaches to an exterior wire end of an adjacent rod.

7. The apparatus of claim 1, wherein the DC power supply outputs from about 5 to about 24 volts DC at from about 1 to about 3 amperes.

8. The apparatus of claim 1, wherein the plurality of rods are disposed substantially parallel to each other.

9. The apparatus of claim 1, further comprising a flexible housing containing the plurality of rods.

10. The apparatus of claim 1, wherein the plurality of rods includes from about 5 to about 20 rods.

11. A method for generating a multi-vibrational electromagnetic field, the method comprising moving current through a plurality of copper wire coils, each of the copper wire coils wrapped around a rod, each of the rods being connected to a flexible spacer strip, and each of the rods being disposed substantially parallel to each other.

12. The method of claim 11, further comprising:
encasing the plurality of rods in a flexible housing; and
wrapping the housing around a pipe.

13. The method of claim 11, further comprising placing the generated electromagnetic field near a person or animal in need thereof in order to treat inflammation or pain.

14. The method of claim 11, further comprising:
encasing the plurality of rods in a flexible housing; and
wrapping the housing around a fuel line.

15. The method of claim 11, further comprising:
wrapping the wire at least once from one end of the non-conductive coating to the other end of the non-conductive coating and back to the original end; and
attaching an inner wire end of one rod to an exterior wire end of an adjacent rod.

16. An electromagnetic apparatus delivering multi-vibrational fields, the electromagnetic apparatus comprising:
a plurality of spaced apart elongated rods with opposing ends, the rods partially covered with a non-conductive coating leaving the opposing ends of the rods uncovered;
copper wire wrapped around each of the plurality of elongated rods, over the non-conductive coating, forming a plurality of copper coils connected in sequence to a power supply;
a flexible spacer strip attached to each end of the elongated rods; and
a flexible housing for containing the plurality of copper coils.

17. The electromagnetic apparatus of claim 16, wherein:
the wire is wrapped at least once from one end of the non-conductive coating to the other end of the non-conductive coating and back to the original end; and
an inner wire end of one rod attaches to an exterior wire end of an adjacent rod.

* * * * *

UNITED STATES PATENT AND TRADEMARK OFFICE
CERTIFICATE OF CORRECTION

PATENT NO. : 8,477,003 B2
APPLICATION NO. : 13/262227
DATED : July 2, 2013
INVENTOR(S) : Gary Dean Wilson and Michael Dean Brown Page 1 of 1

It is certified that error appears in the above-identified patent and that said Letters Patent is hereby corrected as shown below:

In the Claims

Col. 6, Claim 1, Line 18, replace the word "felxible" with "flexible".

Signed and Sealed this
Twenty-fourth Day of September, 2013

Teresa Stanek Rea
*Deputy Director of the United States Patent and Trademark Office*